United States Patent
Holz et al.

(10) Patent No.: US 7,016,034 B2
(45) Date of Patent: Mar. 21, 2006

(54) METHODS OF USING AND FABRICATING A SUPPORTING SUBSTRATE FOR THE DEPOSITION, AUTOMATED RECOGNITION, AND SPECTROSCOPIC IDENTIFICATION OF PARTICLES

(75) Inventors: Lothar Holz, Berlin (DE); Oliver Valet, Berlin (DE); Markus Lankers, Berlin (DE)

(73) Assignee: RAP.ID Particle Systems GmbH, Berlin (DE)

( * ) Notice: Subject to any disclaimer, the term of this patent is extended or adjusted under 35 U.S.C. 154(b) by 0 days.

(21) Appl. No.: 11/229,810

(22) Filed: Sep. 19, 2005

(65) Prior Publication Data

US 2006/0017919 A1    Jan. 26, 2006

Related U.S. Application Data

(62) Division of application No. 10/478,588, filed as application No. PCT/EP02/05769 on May 24, 2002.

(30) Foreign Application Priority Data

May 31, 2001  (DE)  ................... 101 27 537

(51) Int. Cl.
   *G01J 3/44*   (2006.01)
   *G01N 21/65*  (2006.01)
(52) U.S. Cl. ...................................... 356/301
(58) Field of Classification Search ............ 356/301
   See application file for complete search history.

(56) References Cited

U.S. PATENT DOCUMENTS 5,255,067 A  * 10/1993 Carrabba et al. ........... 356/301
6,226,082 B1 *  5/2001 Roe ............................ 356/301

* cited by examiner

*Primary Examiner*—F. L. Evans
(74) *Attorney, Agent, or Firm*—Hahn Loeser & Parks LLP

(57) ABSTRACT

Methods of fabricating and using a supporting substrate for the deposition, automated recognition and spectroscopic identification of particulate impurities in liquid or gaseous media are disclosed wherein the supporting substrate comprises a filter membrane of polymer materials of a defined pore width, wherein the surface of the filter membrane is coated with metal which in the selected wavelength range for spectroscopic identification has no spectral features and at the selected excitation wavelength absorbs no or only little of the laser energy which is radiated in, and has a very smooth structure.

11 Claims, 2 Drawing Sheets

METHODS OF USING AND FABRICATING A SUPPORTING SUBSTRATE FOR THE DEPOSITION, AUTOMATED RECOGNITION, AND SPECTROSCOPIC IDENTIFICATION OF PARTICLES

CROSS-REFERENCE TO RELATED APPLICATIONS/INCORPORATION BY REFERENCE

This patent application is a division of U.S. patent application Ser. No. 10/478,588 having a filing date of Jun. 7, 2004 and which is the national stage of International Application PCT/EP02/05769 having an international filing date of May 24, 2002 and which is based off of German Patent Application DE 101 27 537.4 filed on May 31, 2001.

TECHNICAL FIELD

Certain embodiments of the present invention relate to methods associated with a supporting substrate for the deposition, automated recognition and spectroscopic identification of particles, in particular, particulate impurities and, in particular, for use with Raman spectroscopy.

BACKGROUND OF THE INVENTION

Different methods are known for the deposition of solid particulate impurities from air or liquids. The simplest methods are based on the deposition of the particles on filter membranes both in gaseous and also liquid media with subsequent analysis by means of suitable methods such as light microscopy, scanning electron microscopy or gravimetric analysis (see for example Millipore Particle Monitoring Guide, Millipore Corporation, 1998).

The filter membranes generally comprise polymeric materials, such as for example nitrocellulose, nylon, FTFE or PVC, of an exactly defined pore size, wherein the particles of larger diameter than the pore width of the filter accumulate on the latter and can subsequently be analysed. In recent times, for many applications in the area of microelectronics, ascertaining and analysing particularly small particles, so-called micro-particles, in the range of sizes of about 10 $\mu$m or less, is of particular interest, the analysis of which is problematical with the hitherto known methods, by virtue of the size relationships of the particles to be analyzed.

Metal filters are also known, such as for example metal filters consisting of silver, for filtration purposes, from Millipore, which however because of their method of manufacture have a surface which, by virtue of its roughness, is not suitable for the recognition or identification of individual particles of <5 $\mu$m. The corporation alto tec GmbH of Hamburg offers gold-plated filters for determining asbestos concentrations, which are also not optimized for the described use.

Procedures exist for the quantitative contamination analysis of smooth surfaces, such procedures using a laser beam and a laser scanner for scanning surfaces and detecting deviations from a plane by means of the scattered light which is collected with a photodetector. Such a method is set forth in U.S. Pat. No. 5,479,252. It is however not possible to implement chemical characterization of the particles with that method.

Other methods, such as that set forth, for example, in U.S. Pat. No. 6,178,383, investigate video images in digital form with image recognition programs and, besides the recognition of particulate impurities, can also provide information about the shape and/or size thereof. The equipment for methods of that kind however is very costly in comparison with the laser technology, and also identification of the particles with that method is not possible. The resolution of those methods is admittedly theoretically only diffraction-limited but it is difficult to determine the size of particles which are smaller than 1.5 $\mu$m.

Methods of Raman spectroscopy are known for the qualitative and quantitative analysis of the composition of a sample, in particular of microparticles (M Lankers, J Popp, G Rössling and W Kiefer, Chem Phys Let 277 (1997) 331–334) and have proven to be advantageous. In that case, a sample is irradiated with intensive electromagnetic monochromatic radiation, for example laser light. For that purpose, electromagnetic radiation from the visible or ultraviolet spectral range is usually employed. Upon measurement of the scattered light with a spectrometer and a suitable detector, that is to say when determining the beam intensity of the scattered light as a function of wavelength, the result obtained is a spectrum which comprises a strong line, the so-called exciter line, and very many weaker lines, the so-called Raman lines. The exciter line has the same wave number as the incident radiation. The Raman lines respectively correspond to specific rotational or vibrational states of the substance to be investigated. The Raman lines are arranged on a wave number scale symmetrically with respect to the exciter line. In addition the Raman lines are of an intensity which is between $10^{-3}$ and $10^{-4}$ times less, with the intensity of the Raman lines on the low-frequency side usually being substantially greater at ambient temperature than those on the higher-frequency side.

The Raman spectrum, that is to say the sequences of Raman lines, is characteristic in respect of each substance. A compound can be identified by comparison of its spectrum with the spectra of known compounds.

It will be noted however that the low level of efficiency of Raman spectroscopy is found to be problematical when using that procedure. It is necessary to use very high laser powers for investigating small amounts of substances, as is the case when investigating microparticles. In that respect it is undesirable that the focus of the laser beam is generally markedly larger than the diameter of the particle. Thus there is the unwanted consequence that the signal of the supporting substrate is recorded at the same time and in that situation the spectrum of the particle is slightly overlapped. That becomes clear from the area relationships. If a focus of about 10 $\mu$m in diameter is used in order to investigate a particle of a diameter of 1 $\mu$m, the supporting substrate/particle signal relationship is about 10:1. In most cases that makes it impossible to characterize the particle. In some cases it is possible to resolve the problem by focusing the laser beam to 1 $\mu$m. In that situation however the energy density rises severely and results in damage or a modification as a consequence of burning or photochemical reactions on the part of sensitive substances.

Therefore, certain embodiments of the present invention provide supporting substrates for the spectroscopic analysis of particles, preferably Raman spectroscopy, which reduce the above-indicated disadvantages, in particular in the analysis of microparticles, to such a degree that reliable analysis results are obtained and which in addition are suitable for the filtration of both liquid and also gaseous media.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

In accordance with an embodiment of the present invention, a supporting substrate is used for the deposition, automated recognition and spectroscopic identification of particulate impurities in liquid or gaseous media, where the supporting substrate comprises a filter membrane of polymer materials of a defined pore width, wherein the surface of the filter membrane is coated with metal which in the selected wavelength range for stereoscopic identification has no spectral features and at the selected excitation wavelength absorbs no or only little of the laser energy which is radiated in, and has a very smooth structure.

Therefore, it is now possible to reliably identify even particulate impurities in the micro range, in particular of between about 1 and 10 μm, by means of spectroscopic analysis, in particular Raman spectroscopy, and to obtain virtually unfalsified analysis results. Focusing of the laser beam on to the particle diameter and therewith a great increase in energy density with the unwanted consequences of damage to or a change in the supporting substrate and/or the particle to be analyzed is no longer required, whereby the range of application of Raman spectroscopy is enlarged and reliable analysis procedures are achieved. The coating with a thin metal layer permits the inexpensive manufacture of supporting substrates, with the advantageous properties of the metals for the selected wavelength ranges still being retained. The metal-coated membranes permit various pore sizes or widths and are suitable for the deposition of the particles both from gaseous and also liquid media.

The fact that the metal layer, in the selected excitation wavelength range, absorbs no or only little of the radiated-in laser energy, avoids destruction of the coating and/or the particle to be analyzed. For example gold-coated filters cannot be used for the investigation of particles in the near-infrared range (700–1070 nm). Power densities of about 80 kW/cm$^2$ are required for investigating the particles. In that range however the gold layers only have a load-carrying capacity of less than 1 kW/cm$^2$. It is however possible to use gold-coated filters in the rest of the spectral range. A further example is represented by a silver coating. Here, no investigation procedures are possible in the range of 350–500 nm with 80 kW/cm$^2$. Aluminum cannot be used in a spectral range of 240–280 nm.

In accordance with an embodiment of the present invention, filter membranes with a very smooth surface (roughness RMS<1 μm) are used, for example polycarbonate, polytetrafluoroethylene, such as that sold commercially by duPont under the trademark TEFLON, or cellulose acetate membranes, with defined pores of for example 0.2; 0.8 or 1.2 μm.

The metal layer comprises, for example, nickel, aluminum, palladium, platinum, tungsten, iron, tantalum, rhodium, cadmium, copper, gold, silver, indium, cobalt, tin, silicon, germanium, tellurium, selenium or an alloy of those metals. The thickness of the coating is, in accordance with an embodiment of the present invention, between 50 and 200 nm.

The supporting substrates, according to certain embodiments of the present invention, are particularly suitable for Raman spectroscopy, but also for other spectral analysis methods.

These and other advantages and novel features of the present invention, as well as details of illustrated embodiments thereof, will be more fully understood from the following description and drawings.

BRIEF DESCRIPTION OF SEVERAL VIEWS OF THE DRAWINGS

The invention is described in greater detail hereinafter by means of embodiments with reference to the accompanying drawings in which.

DETAILED DESCRIPTION OF THE INVENTION

For the experiment laser of a wavelength of 785 nm is used, for example a TuiOptik Laser. The laser light is coupled into a microscope by means of a mirror and focussed on to the particles with an objective lens, for example a Nikon ULWD 40 lens. The backscattered light is collected by the same objective lens, coupled into a fiber and the exciter wavelength is filtered out by means of a notch filter, for example a supernotch filter (Kaiser Optical). Finally the inelastically scattered light is spectrally divided up in a spectrometer, for example an Acton spectrometer, and the Raman lines are recorded with a detector, for example a Backthinned CCD camera.

Figure 1:
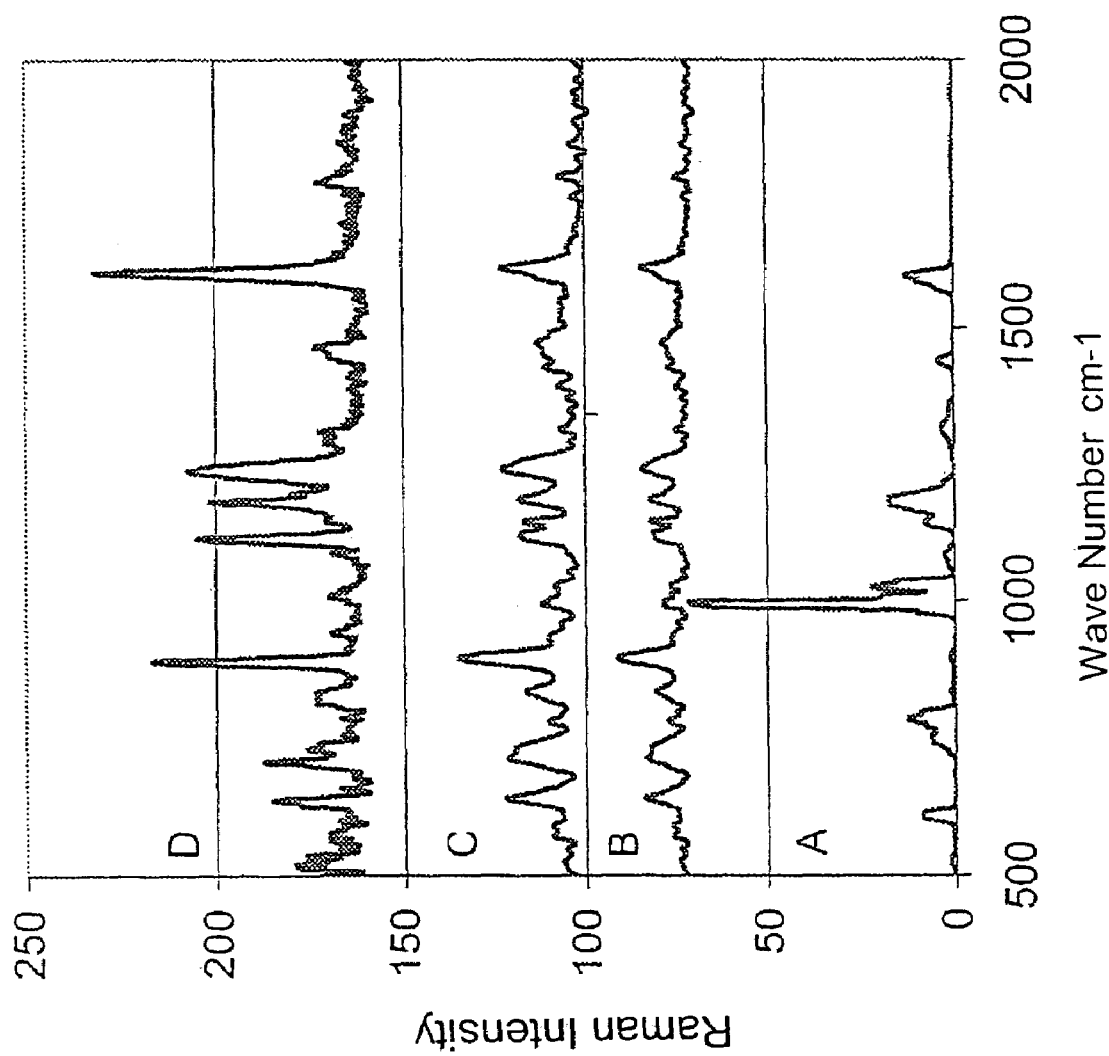
FIG. 1 shows the Raman spectrum of polystyrene beads on an uncoated polycarbonate filter.

FIGS. 1A and 1D respectively illustrate the pure spectra of polystyrene, the particle to be analyzed, and polycarbonate, the filter membrane. FIG. 1B shows the spectrum of a polystyrene bead of a diameter of 3 μm which is disposed on an uncoated polycarbonate membrane. The focus of the laser beam with which this investigation was implemented is of a diameter of about 10 μm. In practice only spectral features of the filter material are to be recognized, identification of the material to be analyzed is practically impossible (see 1A, 1D). FIG. 1C shows the spectrum of the same particle upon irradiation with a narrow laser focus of about 1 μm. The spectral components of the polystyrene beads can only be weakly recognized. The overall spectrum however is still strongly dominated by the features of the filter material.

The following comparative example involves the use of a polycarbonate filter of 25 mm diameter and a pore diameter of 0.8 μm which, in accordance with an embodiment of the present invention, is vapor-deposited with aluminum in a layer thickness of 100 nm.

Figure 2:
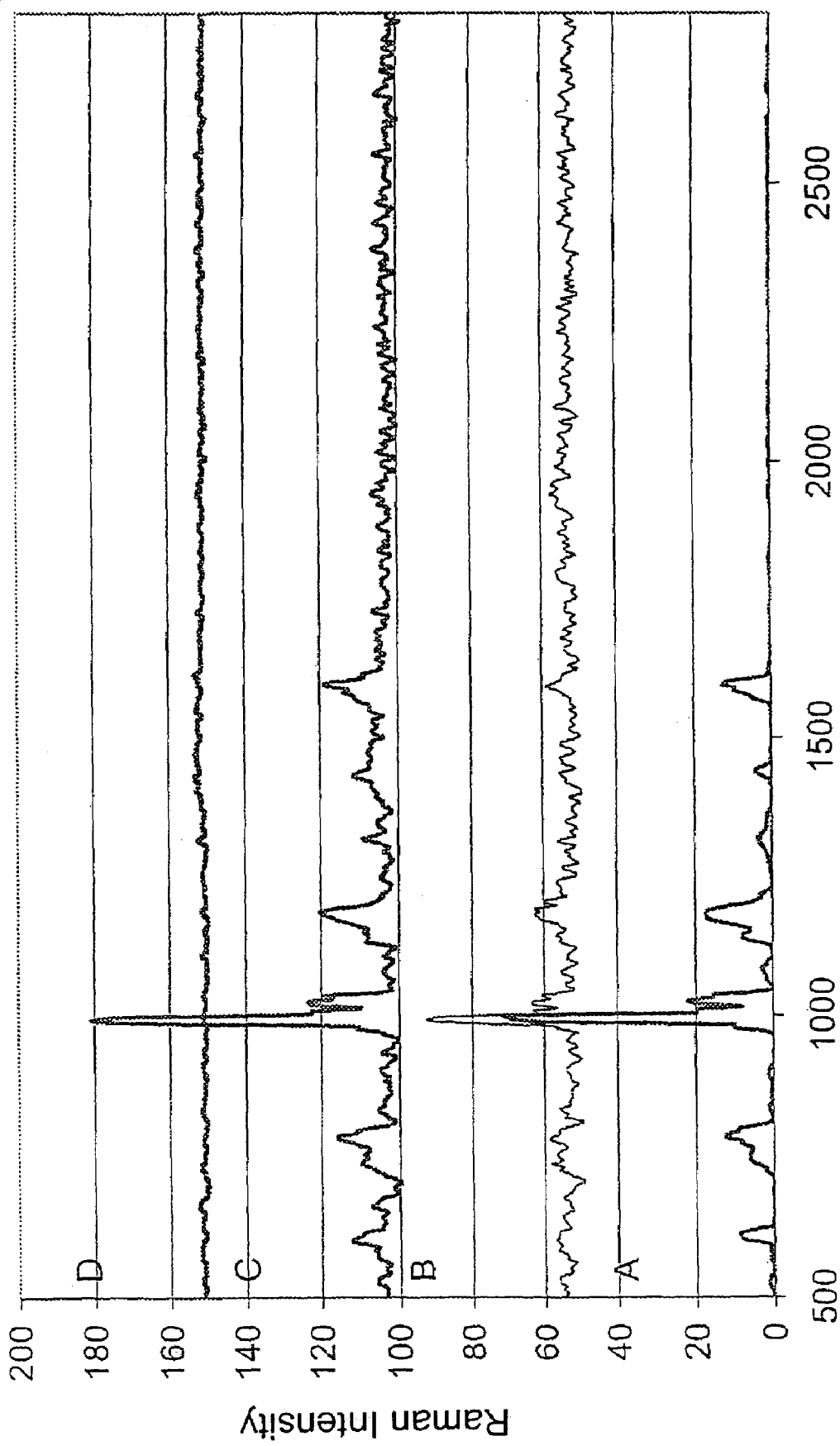
FIG. 2 shows the Raman spectrum of polystyrene beads on a polycarbonate filter coated in accordance with an embodiment of the present invention.

In comparison with the above-illustrated spectra FIG. 2D shows the spectrum of pure polystyrene and the aluminum coating. The spectrum of the coated filter does not have any structure whatsoever. The spectrum of the polystyrene beads of a diameter of 3 μm, illuminated with a 10 μm laser focus but on an aluminum vapor-deposited filter is to be seen from FIG. 2B. No falsifying bands on the part of the polycarbonate are to be recognized. The essential spectral features of the particle to be analyzed are to be seen so that unambiguous identification is now possible. The same effect can also be observed for analysis of the particle with a focus of 1 μm, see FIG. 2C. Most spectral features of the comparative spectrum can be found again here.

The example makes it clear that identification of small particles by Raman spectroscopy on commercially available filter membranes with laser foci in the range of 2–10 μm is not possible. A marked improvement in identification is achieved with the filter membranes coated in accordance with an embodiment of the present invention.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for identifying particles, said method comprising:
    depositing at least one particle from a gaseous or liquid media onto a supporting substrate wherein said supporting substrate comprises a filter membrane of polymer materials of a defined pore width, and wherein said filter membrane includes a surface coated with a metal layer that has no spectral features in a wavelength range selected for spectroscopic identification and that absorbs no or only little of the laser energy which is radiated in at a selected excitation wavelength, the surface coating having a thickness of between about 50 and 200 nm, and having a very smooth structure with a roughness of less than 1 $\mu$m;
    focusing said laser energy of said selected exciter wavelength onto said at least one deposited particle as part of said spectroscopic identification;
    collecting backscattered light from said at least one deposited particle;
    filtering out said at least one exciter wavelength from said collected light;
    generating a spectrum of said filtered light using spectroscopic analysis techniques; and
    identifying a chemical composition of said at least one deposited particle in response to said generated spectrum.

2. The method of claim 1 wherein said metal layer is selected from the group consisting of: nickel, aluminum, palladium, platinum, tungsten, iron, tantalum, rhodium, cadmium, copper, gold, silver, indium, cobalt, tin, silicon, germanium, tellurium, selenium and alloys thereof.

3. The method of claim 1 wherein said metal layer is vapor-deposited.

4. The method of claim 1 wherein said filter membrane comprises polycarbonate, polytetrafluoroethylene or cellulose acetate.

5. The method of claim 1 wherein said defined pore width is between about 0.2 and 1.2 $\mu$m.

6. The method of claim 1 wherein said spectroscopic identification is effected by Raman spectroscopy.

7. A method of fabricating a supporting substrate used for the deposition, automated recognition, and spectroscopic identification of particulate impurities in liquid or gaseous media, said method comprising:
    generating a filter membrane of polymer materials of a defined pore width; and
    vapor-depositing a metal layer onto a surface of said filter membrane, and wherein said metal layer has no spectral features in a wavelength range selected for spectroscopic identification and that absorbs no or only little of the laser energy which is radiated in at a selected excitation wavelength, the surface coating having a thickness of between about 50 and 200 nm, and having a very smooth structure with a roughness of less than 1 $\mu$m.

8. The method of claim 7 wherein said metal layer is selected from the group consisting of: nickel, aluminum, palladium, platinum, tungsten, iron, tantalum, rhodium, cadmium, copper, gold, silver, indium, cobalt, tin, silicon, germanium, tellurium, selenium and alloys thereof.

9. The method of claim 7 wherein said filter membrane comprises polycarbonate, polytetrafluoroethylene or cellulose acetate.

10. The method of claim 7 wherein said defined pore width is between about 0.2 and 1.2 $\mu$m.

11. The method of claim 7 wherein said spectroscopic identification is effected by Raman spectroscopy.

* * * * *